US007468473B1

(12) United States Patent
Peng

(10) Patent No.: US 7,468,473 B1

(45) Date of Patent: Dec. 23, 2008

(54) LETTUCE CULTIVAR TRUE HEART

(75) Inventor: Yaojin Peng, Salinas, CA (US)

(73) Assignee: Synergene Seed & Technology, Inc., Salinas, CA (US)

( * ) Notice: Subject to any disclaimer, the term of this patent is extended or adjusted under 35 U.S.C. 154(b) by 0 days.

(21) Appl. No.: 11/966,344

(22) Filed: Dec. 28, 2007

(51) Int. Cl.
*A01N 1/00* (2006.01)
*A01H 4/00* (2006.01)
*A01H 5/00* (2006.01)
*A01H 5/10* (2006.01)
*C12N 15/82* (2006.01)

(52) U.S. Cl. ....................... 800/305; 435/410; 800/260; 800/278; 800/279; 800/298; 800/300; 800/301; 800/302; 800/303

(58) Field of Classification Search ....................... None
See application file for complete search history.

(56) References Cited

U.S. PATENT DOCUMENTS 5,304,719 A 4/1994 Segebart
5,367,109 A 11/1994 Segebart
5,523,520 A 6/1996 Hunsperger et al.
5,763,755 A 6/1998 Carlone
5,850,009 A 12/1998 Kevern

OTHER PUBLICATIONS

Bassett, et al., 1975. The role of leaf shape in the inheritance of heading in lettuce, J. Am. Soc. Hortic. Sci. 100(2):104-105.

Bennetzen, et al., 1992. Approaches and progress in the molecular cloning of plant disease resistance genes, *In* Genetic Engineering. 14:99-124, Ed. J.K. Setlow, Plenum Press, NY.

DeBolle, et al., 1996. Antimicrobial peptides from *Mirabilis jalapa and Amaranthus caudatus*: expression, processing, localization and biological activity in transgenic tobacco. Plant Molec. Biol. 31:993-1008.

DeVries, et al., 1994. Numerical morphological analysis of lettuce cultivars and species (*Lactuca* sect. *Lactuca, Asteracea*). Pl. Syst. Evol. 193:125-141.

Eshed, et al, 1996. Less-than-additive epistatic interactions of quantitative trait loci in tomato. Genetics 143:1807-1817.

Kraft, et al, 2000. Linkage disequilibrium and fingerprinting in sugar beet. Theor. Appl. Genet. 101:323-326.

Michelmore, et al, 1987. Transformation of lettuce (*Lactuca sativa*) mediated by *Agrobacterium tumefaciens*. Plant Cell Rep. 6:439-442.

Pang, et al., 1992. Expression of a gene encoding a scorpion insectotoxin peptide in yeast, bacteria and plants. Gene 116:165-172.

Ryder, et al., 1992. Lettuce genetics: Inheritance, linkage and epistasis. J. Amer. Soc. Hort. Sci. 117(3):504-507.

Ryder, et al, 1999. Inheritance and epistasis studies of chlorophyll deficiency in lettuce. J. Amer. Soc. Hort. Sci. 124(6):636-640.

Thomas, et al., 1974. Lettuce production in the United States, *In* Agriculture Handbook No. 221. Agricultural Research Service of the United States Department of Agriculture. pp. 4-5.

Waycott, et al., 1994. Differentiation of nearly identical germplasm accessions by a combination of molecular and morphologic analyses. Genome 37(4):577-583.

Xinrun and Conner, 1992. Genotypic effects on tissue culture response of lettuce cotyledons, J. Genet. & Breed. 46:287-290.

*Primary Examiner*—David H Kruse
(74) *Attorney, Agent, or Firm*—Jondle & Associates, P.C.

(57) ABSTRACT

A novel romaine lettuce cultivar, designated True Heart, is disclosed. The invention relates to the seeds of lettuce cultivar True Heart, to the plants of lettuce cultivar True Heart and to methods for producing a lettuce plant by crossing the cultivar True Heart with itself or another lettuce cultivar. The invention further relates to methods for producing a lettuce plant containing in its genetic material one or more transgenes and to the transgenic plants produced by that method and to methods for producing other lettuce cultivars derived from the cultivar True Heart.

22 Claims, No Drawings

LETTUCE CULTIVAR TRUE HEART

BACKGROUND OF THE INVENTION

The present invention relates to a new and distinctive Romaine lettuce (*Lactuca sativa*) cultivar, designated True Heart. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Practically speaking, all cultivated forms of lettuce belong to the highly polymorphic species *Lactuca sativa* that is grown for its edible head and leaves. As a crop, lettuces are grown commercially wherever environmental conditions permit the production of an economically viable yield. Lettuce is the world=s most popular salad. In the United States, the principal growing regions are California and Arizona which produce approximately 287,000 acres out of a total annual acreage of more than 300,000 acres (USDA, 2001). Fresh lettuces are available in the United States year-round although the greatest supply is from May through October. For planting purposes, the lettuce season is typically divided into three categories, early, mid and late, with the coastal areas planting from January to August, and the desert regions from August to December. Fresh lettuces are consumed nearly exclusively as fresh, raw product, occasionally as a cooked vegetable.

*Lactuca sativa* is in the Cichoreae tribe of the Asteraceae (Compositae family). Lettuce is related to chicory, sunflower, aster, dandelion, artichoke and chrysanthemum. Sativa is one of about 300 species in the genus *Lactuca*. There are seven different morphological types of lettuces. The Crisphead group includes the iceberg and batavian types. Iceberg lettuce has a large, firm head with a crisp texture and a white or creamy yellow interior. Batavian lettuce predates the iceberg type and has a smaller and less firm head. The Butterhead group has a small, soft head with an almost oily texture. Romaine lettuce, also known as cos lettuce, has elongated upright leaves forming a loose, loaf shaped head. The outer leaves are usually dark green. The Leaf lettuces come in many varieties, none of which form a head. The next three types are seldom seen in the United States: Latin lettuce looks like a cross between romaine and butterhead; stem lettuce has long, narrow leaves and thick, edible stems, and Oilseed lettuce is a type grown for its large seeds that are pressed to obtain oil.

*Lactuca sativa* is a simple diploid species with nine pairs of chromosomes. Lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is tedious. As such, a modified method of misting to wash the pollen off prior to fertilization is needed to assure crossing or hybridization. About 60-90 min past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen grains are washed off with enough pressure to dislodge the pollen grains, but not enough to damage the style. Excess water is dried off with clean paper towels. About 30 min later the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.). Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection. These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of lettuce plant breeding is to develop new, unique and superior lettuce cultivars. The breeder initially selects and crosses two or more parental cultivars, followed by repeated selfing and selection, producing many new genetic combinations. The breeder can theoretically generate billions of different genetic combinations via crossing, selfing and mutations. The breeder has no direct control at the cellular level.

Therefore, two breeders will never develop the same cultivar, or even very similar cultivars, having the same lettuce traits.

Each year, the plant breeder selects the germplasm to advance to the next generation. This germplasm is grown under unique and different geographical, climatic and soil conditions and further selections are then made, during and at the end of the growing season. The cultivars that are developed are unpredictable because the breeder's selection occurs in unique environments, with no control at the DNA level (using conventional breeding procedures), and with millions of different possible genetic combinations being generated. A breeder of ordinary skill in the art cannot predict the final resulting cultivars he develops, except possibly in a very gross and general fashion. The same breeder cannot produce the same cultivar twice by using the exact same original parents and the same selection techniques. This unpredictability results in the expenditure of large research monies to develop superior lettuce cultivars.

The development of commercial lettuce cultivars requires the development of lettuce varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred cultivars of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best cultivars or mixtures of phenotypically similar cultivars are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which cultivars are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (e.g., "Principles of Plant Breeding" John Wiley and Son, pp. 115-161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Lettuce in general and romaine lettuce in particular is an important and valuable vegetable crop. Thus, a continuing goal of lettuce plant breeders is to develop stable, high yielding lettuce cultivars that are agronomically sound. To accomplish this goal, the lettuce breeder must select and develop lettuce plants with traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

According to the invention, there is provided a novel romaine lettuce cultivar designated True Heart. This invention thus relates to the seeds of lettuce cultivar True Heart, to the plants of lettuce cultivar True Heart and to methods for producing a lettuce plant produced by crossing the lettuce True Heart with itself or another lettuce cultivar, and to methods for producing a lettuce plant containing in its genetic material one or more transgenes and to the transgenic lettuce plants produced by that method. This invention also relates to methods for producing other lettuce cultivars derived from lettuce cultivar True Heart and to the lettuce cultivar derived by the use of those methods. This invention further relates to hybrid lettuce seeds and plants produced by crossing the cultivar True Heart with another lettuce cultivar.

In another aspect, the present invention provides regenerable cells for use in tissue culture of lettuce cultivar True Heart. The tissue culture will preferably be capable of regenerating plants having the physiological and morphological characteristics of the foregoing lettuce plant, and of regenerating plants having substantially the same genotype as the foregoing lettuce plant. Preferably, the regenerable cells in such tissue cultures will be embryos, protoplasts, seeds, callus, pollen, leaves, anthers, pistils, roots, root tips and meristematic cells. Still further, the present invention provides lettuce plants regenerated from the tissue cultures of the invention.

Another aspect of the invention is to provide methods for producing other lettuce plants derived from lettuce cultivar True Heart. Lettuce cultivars derived by the use of those methods are also part of the invention.

The invention also relates to methods for producing a lettuce plant containing in its genetic material one or more transgenes and to the transgenic lettuce plant produced by that method.

In another aspect, the present invention provides for single gene converted plants of True Heart. The single transferred gene may preferably be a dominant or recessive allele. Preferably, the single transferred gene will confer such traits as male sterility, herbicide resistance, insect resistance, resistance for bacterial, fungal, or viral disease, male fertility, enhanced nutritional quality and industrial usage. The single gene may be a naturally occurring lettuce gene or a transgene introduced through genetic engineering techniques.

The invention further provides methods for developing lettuce plants in a lettuce plant breeding program using plant breeding techniques including recurrent selection, backcrossing, pedigree breeding, restriction fragment length polymorphism enhanced selection, genetic marker enhanced selection and transformation. Seeds, lettuce plants, and parts thereof produced by such breeding methods are also part of the invention.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. The allele is any of one or more alternative form of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having essentially all of the physiological and morphological characteristics of the recurrent parent, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of a cultivar are recovered in addition to the single gene transferred into the cultivar via the backcrossing technique or via genetic engineering.

Maturity Date. Maturity refers to the stage when the plants are of full size or optimum weight, in marketable form or shape to be of commercial or economic value. In romaine types they range from 50-75 days from time of seeding, depending upon the season of the year.

RHS. RHS refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK.

Yield (Tons/Acre). The yield in tons/acre is the actual yield of the lettuce at harvest.

DETAILED DESCRIPTION OF THE INVENTION

Lettuce cultivar True Heart has superior characteristics and was developed from the cross made in 2000 of PIC 714, a proprietary romaine breeding line, and Green Forest (U.S. Pat. No. 6,649,815). Six $F_1$ hybrids were grown in a greenhouse during the fall of 2000. 400 $F_2$ plants were established in the spring of 2001 in Salinas, California and 12 individual plants were selected. In the spring of 2002 nine $F_3$ families were planted and 21 individuals were selected from six of the nine $F_3$ families. In the spring of 2003, 21 $F_4$ families were established and 40 individual plants were selected from 13 of the 21 $F_4$ families. In the spring of 2004,14 $F_5$ lines were established and 24 individual plants were selected from seven of the 14 $F_5$ lines. In the spring of 2005 15 $F_6$ lines were planted, line 05BS-0943 showed high uniformity and very desirable horticultural characteristics. In the summer of 2005, line 05BS-0943 was planted in a seed increase nursery in the San Joaquin Valley and seeds were harvested. The line 05BS-0943 became lettuce cultivar True Heart.

True Heart is a romaine lettuce with a medium-green leaf color, thick and moderate blistered leaf texture, moderately firm and slightly V-shaped head; it is widely adoptable in a variety of environments. True Heart is highly resistant to tipburn, Schlertinia rot and brown rib. True Heart has shown a very good adaptability in the California and Arizona regions of the United States.

Some of the criteria used for selection in various generations include: color, disease resistance, head weight, number of leaves, appearance and length, yield, emergence, maturity, plant architecture, seed yield and quality.

The cultivar has shown uniformity and stability for the traits, within the limits of environmental influence for the traits. It has been self-pollinated a sufficient number of generations with careful attention to uniformity of plant type. The cultivar has been increased with continued observation for uniformity. No variant traits have been observed or are expected in True Heart.

Lettuce cultivar True Heart has the following morphologic and other characteristics (based primarily on data collected at Salinas, Calif.).

TABLE 1

| VARIETY DESCRIPTION INFORMATION |
| --- |
| Plant Type: Romaine |
| Seed: |
| Color: Black |
| Light dormancy: Light not required |
| Heat dormancy: Susceptible |
| Cotyledon to Fourth Leaf Stage: |
| Shape of cotyledons: Broad |
| Undulation: Flat |
| Anthocyanin distribution: Absent |
| Rolling: Absent |

TABLE 1-continued

| VARIETY DESCRIPTION INFORMATION |
| --- |
| Cupping: Uncupped |
| Reflexing: None |
| Mature Leaves: |
| Margin - Incision depth: Absent/Shallow |
| Margin - Indentation: Absent/Slight |
| Green color: Medium-green |
| Anthocyanin - Distribution: Absent |
| Size: Medium |
| Glossiness: Dull |
| Blistering: Moderate |
| Trichomes: Absent |
| Leaf thickness: Thick |
| Plant at Market Stage: |
| Head shape: Slight V-shaped |
| Head size class: Medium |
| Head weight: 788 g |
| Head firmness: Moderate |
| Core: |
| Diameter at base of head: 3.77 cm |
| Core height from base of head to apex: 6.49 cm |
| Maturity: |
| Summer: 55 days |
| Winter: 95 days |
| Adaptation: |
| Primary Regions of Adaptation (tested and proven adapted) |
| Southwest (California, Arizona desert): Adapted |
| West Coast: Adapted |
| Southeast: N/A |
| Northeast: N/A |
| Spring area: San Joaquin, CA, Imperial, CA; Yuma, AZ |
| Summer area: Salinas, CA, Santa Maria, CA, San Benito, CA |
| Fall area: Salinas, CA, Santa Maria, CA, Oxnard, CA |
| Winter area: Yuma, AZ; Imperial, CA, Coachella, CA |
| Greenhouse: N/A |
| Soil Type: Both Mineral and Organic |
| Disease and Stress Reactions: |
| Virus: |
| Big Vein: Intermediate |
| Lettuce Mosaic: Susceptible |
| Cucumber Mosaic: Not tested |
| Broad Bean Wilt: Not tested |
| Turnip Mosaic: Not tested |
| Best Western Yellows: Not tested |
| Lettuce Infectious Yellows: Not tested |
| Fungal/Bacterial: |
| Corky Root Rot (Pythium Root Rot): Intermediate |
| Downy Mildew: Susceptible |
| Powdery Mildew: Susceptible |
| Sclerotinia Rot: Highly resistant |
| Bacterial Soft Rot (*Pseudomonas* sp. & others): Not tested |
| Botrytis (Gray Mold): Susceptible |
| Insects: |
| Cabbage Loopers: Susceptible |
| Root Aphids: Susceptible |
| Green Peach Aphid: Susceptible |
| Physiological/Stress: |
| Tipburn: Highly resistant |
| Heat: Intermediate |
| Drought: Not tested |
| Cold: Resistant |
| Salt: Not tested |
| Brown Rib: Highly resistant |
| Post Harvest: |
| Pink Rib: Resistant |
| Russet Spotting: Not tested |
| Rusty Brown Discoloration: Resistant |
| Internal Rib Necrosis (Blackhead, Gray Rib, Gray Streak): Resistant |
| Brown Stain: Not tested |

FURTHER EMBODIMENTS OF THE INVENTION

This invention also is directed to methods for producing a lettuce cultivar plant by crossing a first parent lettuce plant with a second parent lettuce plant wherein either the first or second parent lettuce plant is a lettuce plant of the cultivar True Heart. Further, both first and second parent lettuce plants can come from the cultivar True Heart. Still further, this invention also is directed to methods for producing a cultivar True Heart-derived lettuce plant by crossing cultivar True Heart with a second lettuce plant and growing the progeny seed, and repeating the crossing and growing steps with the cultivar True Heart-derived plant from 0 to 7 times. Thus, any such methods using the cultivar True Heart are part of this invention: selfing, backcrosses, hybrid production, crosses to populations, and the like. All plants produced using cultivar True Heart as a parent are within the scope of this invention, including plants derived from cultivar True Heart. Advantageously, the cultivar is used in crosses with other, different, cultivars to produce first generation ($F_1$) lettuce seeds and plants with superior characteristics.

As used herein, the term plant includes plant cells, plant protoplasts, plant cell tissue cultures from which lettuce plants can be regenerated, plant calli, plant clumps and plant cells that are intact in plants or parts of plants, such as embryos, pollen, ovules, flowers, seeds, roots, anthers, pistils and the like.

As is well known in the art, tissue culture of lettuce can be used for the in vitro regeneration of a lettuce plant. Tissue culture of various tissues of leftuces and regeneration of plants therefrom is well known and widely published. For example, reference may be had to Teng et al., *HortScience.* 1992, 27: 9,1030-1032, Teng et al., *HortScience.* 1993, 28: 6, 669-1671, Zhang et al., *Journal of Genetics and Breeding.* 1992, 46: 3, 287-290, Webb et al., *Plant Cell Tissue and Organ Culture.* 1994, 38: 1, 77-79, Curtis et al., *Journal of Experimental Botany.* 1994, 45: 279,1441-1449, Nagata et al., *Journal for the American Society for Horticultural Science.* 2000,125: 6, 669-672. It is clear from the literature that the state of the art is such that these methods of obtaining plants are "conventional" in the sense that they are routinely used and have a very high rate of success. Thus, another aspect of this invention is to provide cells which upon growth and differentiation produce lettuce plants having the physiological and morphological characteristics of variety True Heart.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed line.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed lettuce plants, using transformation methods as described below to incorporate transgenes into the genetic material of the lettuce plant(s).

Expression Vectors for Lettuce Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals which confers resistance to kanamycin (Fraley et al., *Proc. Natl. Acad. Sci. U.S.A.,* 80:4803 (1983)). Another commonly used selectable marker gene is the hygromycin phosphotransferase gene which confers resistance to the antibiotic hygromycin (Vanden Elzen et al., *Plant Mol. Biol.,* 5:299 (1985)).

Additional selectable marker genes of bacterial origin that confer resistance to antibiotics include gentamycin acetyl transferase, streptomycin phosphotransferase, aminoglycoside-3'-adenyl transferase, the bleomycin resistance determinant (Hayford et al., *Plant Physiol.* 86:1216 (1988), Jones et al., *Mol. Gen. Genet.,* 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation that are not of bacterial origin include, for example, mouse dihydrofolate reductase, plant 5-enolpyruvyishikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci. U.S.A.* 84:131 (1987), DeBlock et al., *EMBO J.* 3:1681 (1984)).

In vivo methods for visualizing GUS activity that do not require destruction of plant tissues are available (Molecular Probes publication 2908, IMAGENE GREEN, p. 1-4 (1993) and Naleway et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263:802 (1994)). GFP and mutants of GFP may be used as screenable markers.

Expression Vectors for Lettuce Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in lettuce. Optionally, the inducible promoter is operably linked to a nucleotide sequence encoding a signal sequence which is operably linked to a gene for expression in lettuce. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen. Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in lettuce or the constitutive promoter is operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO 96/30530.

C. Tissue-Specific or Tissue-Preferred Promoters

A tissue-specific promoter is operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Nat. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499-509 (1984), Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is lettuce. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US 93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO 95/16776 (disclosure of peptide derivatives of tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum.*

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

S. A lettuce mosaic potyvirus (LMV) coat protein gene introduced into *Lactuca sativa* in order to increase its resistance to LMV infection. See Dinant et al., *Molecular Breeding.* 1997, 3: 1, 75-86.

2. Genes That Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in *Transgenic Research.* 1999, 8: 1, 33-44 that discloses *Lactuca sativa* resistant to glufosinate. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes That Confer or Contribute to a Value-Added Trait, Such as:

A. Increased iron content of the lettuce, for example by transforming a plant with a soybean ferritin gene as described in Goto et al., *Acta Horticulturae.* 2000, 521,101-109.

B. Decreased nitrate content of leaves, for example by transforming a lettuce with a gene coding for a nitrate reductase. See for example Curtis et al., *Plant Cell Report.* 1999, 18: 11, 889-896.

C. Increased sweetness of the lettuce by transferring a gene coding for monellin that elicits a flavor 100,000 times sweeter than sugar on a molar basis. See Penarrubia et al., *Biotechnology.* 1992, 10: 561-564.

D. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

E. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

Methods for Lettuce Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation

One method for introducing an expression vector into plants is based on the natural transformation system of *Agrobacterium*. See, for example, Horsch et al., *Science* 227:1229 (1985), Curtis et al., *Journal of Experimental Botany.* 1994, 45: 279, 1441-1449, Torres et al., *Plant cell Tissue and Organic Culture.* 1993, 34: 3, 279-285, Dinant et al., *Molecular Breeding.* 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Russell, D. R., et al. *Pl. Cell. Rep.* 12(3, Jan.), 165-169 (1993), Aragao, F. J. L., et al. *Plant Mol. Biol.* 20(2, Oct.), 357-359 (1992), Aragao, F. J. L., et al. *Pl. Cell. Rep.* 12(9, July), 483-490 (1993). Aragao, *Theor. Appl. Genet.* 93:142-150 (1996), Kim, J.; Minamikawa, *T. Plant Science* 117: 131-138 (1996), Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Saker, M.; Kuhne, *T. Biologia Plantarum* 40(4): 507-514 (1997/98), Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994). See also Chupean et al., *Biotechnology.* 1989, 7: 5, 503-508.

Following transformation of lettuce target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic lettuce line. Alternatively, a genetic trait which has been engineered into a particular lettuce cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Single-Gene Conversions

When the terms lettuce plant, cultivar or lettuce line are used in the context of the present invention, this also includes any single gene conversions of that line. The term "single gene converted plant" as used herein refers to those lettuce plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental lettuce plants for that line, backcrossing 1, 2, 3, 4, 5, 6, 7, 8 or more times to the recurrent parent. The parental lettuce plant which contributes the gene for the desired characteristic is termed the nonrecurrent or donor parent. This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a lettuce plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196, 5,948,957 and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Teng et al., *HortScience.* 1992, 27: 9, 1030-1032 Teng et al., *HortScience.* 1993, 28: 6, 669-1671, Zhang et al., *Journal of Genetics and Breeding.* 1992, 46: 3, 287-290, Webb et al., *Plant Cell Tissue and Organ Culture.* 1994, 38: 1, 77-79, Curtis et al., *Journal of Experimental Botany.* 1994, 45: 279, 1441-1449, Nagata et al., *Journal for the American Society for Horticultural Science*. 2000, 125: 6, 669-672, and Ibrahim et al., *Plant Cell, Tissue and Organ Culture*. (1992), 28(2): 139-145. It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of variety True Heart.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a lettuce plant by crossing a first parent lettuce plant with a second parent lettuce plant wherein the first or second parent lettuce plant is a lettuce plant of cultivar True Heart. Further, both first and second parent lettuce plants can come from lettuce cultivar True Heart. Thus, any such methods using lettuce cultivar True Heart are part of this invention: selfing, backcrosses, hybrid production, crosses to populations, and the like. All plants produced using lettuce cultivar True Heart as at least one parent are within the scope of this invention, including those developed from cultivars derived from lettuce cultivar True Heart. Advantageously, this lettuce cultivar could be used in crosses with other, different, lettuce plants to produce the first generation ($F_1$) lettuce hybrid seeds and plants with superior characteristics. The cultivar of the invention can also be used for transformation where exogenous genes are introduced and expressed by the cultivar of the invention. Genetic variants created either through traditional breeding methods using lettuce cultivar True Heart or through transformation of cultivar True Heart by any of a number of protocols known to those of skill in the art are intended to be within the scope of this invention.

The following describes breeding methods that may be used with lettuce cultivar True Heart in the development of further lettuce plants. One such embodiment is a method for developing cultivar True Heart progeny lettuce plants in a lettuce plant breeding program comprising: obtaining the lettuce plant, or a part thereof, of cultivar True Heart, utilizing said plant or plant part as a source of breeding material, and selecting a lettuce cultivar True Heart progeny plant with molecular markers in common with cultivar True Heart and/or with morphological and/or physiological characteristics selected from the characteristics listed in Table 1. Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of lettuce cultivar True Heart progeny lettuce plants, comprising crossing cultivar True Heart with another lettuce plant, thereby producing a population of lettuce plants, which, on average, derive 50% of their alleles from lettuce cultivar True Heart. A plant of this population may be selected and repeatedly selfed or sibbed with a lettuce cultivar resulting from these successive filial generations. One embodiment of this invention is the lettuce cultivar produced by this method and that has obtained at least 50% of its alleles from lettuce cultivar True Heart.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the invention includes lettuce cultivar True Heart progeny lettuce plants comprising a combination of at least two cultivar True Heart traits selected from the group consisting of those listed in Table 1 or the cultivar True Heart combination of traits listed in the Summary of the Invention, so that said progeny lettuce plant is not significantly different for said traits than lettuce cultivar True Heart as determined at the 5% significance level when grown in the same environmental conditions. Using techniques described herein, molecular markers may be used to identify said progeny plant as a lettuce cultivar True Heart progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of lettuce cultivar True Heart may also be characterized through their filial relationship with lettuce cultivar True Heart, as for example, being within a certain number of breeding crosses of lettuce cultivar True Heart. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce cultivar True Heart and its progeny. For example, progeny produced by the methods described herein may be within 1, 2, 3, 4 or 5 breeding crosses of lettuce cultivar True Heart.

As used herein, the term "plant" includes plant cells, plant protoplasts, plant cell tissue cultures from which lettuce plants can be regenerated, plant calli, plant clumps and plant cells that are intact in plants or parts of plants, such as leaves, pollen, embryos, cotyledons, hypocotyl, roots, root tips, anthers, pistils, flowers, seeds, stems and the like.

TABLES

In the tables that follow, the traits and characteristics of lettuce cultivar True Heart are given compared to two commercial romaine lettuce cultivars, Green Thunder and PIC Cos.

Table 2 below shows the mature seed stalk height for True Heart as compared to the seed stalk height for Green Thunder and PIC Cos. Seed stalk height is measured in centimeters. An analysis of variance was performed on the data and is shown below the data. As can be seen from the data in Table 2, True Heart has a significantly shorter mature seed stalk height than either Green Thunder or PIC Cos.

TABLE 2

| Seed Stalk Height (cm) | | |
|---|---|---|
| TRUE HEART | Green Thunder | PIC Cos |
| 79 | 105 | 100 |
| 85 | 107 | 102 |
| 85 | 109 | 100 |
| 76 | 108 | 95 |
| 84 | 100 | 96 |
| 72 | 102 | 105 |
| 87 | 103 | 97 |
| 87 | 111 | 98 |
| 89 | 110 | 99 |
| 79 | 101 | 98 |
| 85 | 102 | 99 |
| 72 | 100 | 100 |
| 75 | 110 | 96 |

Anova: Single Factor
SUMMARY

| Groups | Count | Sum | Average | Variance |
|---|---|---|---|---|
| TRUE HEART | 13 | 1055.000 | 81.154 | 35.308 |
| Green Thunder | 13 | 1368.000 | 105.231 | 16.859 |
| PIC Cos | 13 | 1285.000 | 98.846 | 7.308 |

ANOVA

| Source of Variation | SS | df | MS | F | P-value | F crit |
|---|---|---|---|---|---|---|
| Between Varieties | 4045.077 | 2 | 2022.538 | 102.021 | 0.000 | 3.259 |
| Within Varieties | 713.692 | 36 | 19.825 | | | |
| Total | 4758.769 | 38 | | | | |

Table 3 below shows the seed stalk spread for True Heart as compared to the seed stalk spread for Green Thunder and PIC Cos. Seed stalk spread is measured in centimeters. An analysis of variance was performed on the data and is shown below the data. As can be seen from the data in Table 3, True Heart has a significantly narrower mature seed stalk spread than Green Thunder and PIC Cos.

TABLE 3

| Seed Stalk Spread (cm) | | |
|---|---|---|
| True Heart | Green Thunder | PIC Cos |
| 33 | 37 | 52 |
| 34 | 50 | 45 |
| 35 | 44 | 47 |
| 30 | 45 | 41 |
| 34 | 45 | 48 |
| 35 | 46 | 41 |
| 36 | 38 | 42 |
| 38 | 42 | 47 |
| 38 | 43 | 43 |
| 18 | 46 | 48 |
| 33 | 40 | 44 |
| 30 | 45 | 45 |
| 30 | 44 | 40 |

Anova: Single Factor
SUMMARY

| Groups | Count | Sum | Average | Variance |
|---|---|---|---|---|
| TRUE HEART | 13 | 424.000 | 32.615 | 26.590 |
| Green Thunder | 13 | 565.000 | 43.462 | 12.436 |
| PIC Cos | 13 | 583.000 | 44.846 | 12.141 |

ANOVA

| Source of Variation | SS | df | MS | F | P-value | F crit |
|---|---|---|---|---|---|---|
| Between Varieties | 1166.308 | 2 | 583.154 | 34.191 | 0.000 | 3.259 |
| Within Varieties | 614.000 | 36 | 17.056 | | | |
| Total | 1780.308 | 38 | | | | |

Tables 4 through 8 show data collected at twelve different locations in California and Arizona.

Table 4 below shows the plant weight in grams at harvest maturity of True Heart as compared to Green Thunder and PIC Cos. An analysis of variance was performed on the data and is shown below the data. As can be seen from the data in Table 4, True Heart is significantly heavier in plant weight at harvest maturity than either Green Thunder or PIC Cos.

TABLE 4

| | Loc. 1 | Loc. 2 | Loc. 3 | Loc. 4 | Loc. 5 | Loc. 6 | Loc. 7 | Loc. 8 | Loc. 9 | Loc. 10 | Loc. 11 | Loc. 12 |
|---|---|---|---|---|---|---|---|---|---|---|---|---|
| Plant Weight in grams | | | | | | | | | | | | |
| Trail Location: | | | | | | | | | | | | |
| TRUE HEART | 730 | 690 | 880 | 830 | 1020 | 930 | 690 | 650 | 650 | 570 | 720 | 810 |
| | 860 | 950 | 790 | 780 | 930 | 1130 | 680 | 640 | 780 | 750 | 830 | 870 |
| | 730 | 810 | 670 | 970 | 1190 | 890 | 560 | 740 | 730 | 620 | 690 | 640 |
| | 950 | 750 | 960 | 890 | 1130 | 1190 | 610 | 760 | 690 | 630 | 760 | 620 |
| | 850 | 840 | 740 | 860 | 770 | 880 | 480 | 600 | 710 | 720 | 680 | 580 |
| | 760 | 790 | 800 | 760 | 890 | 890 | 620 | 750 | 730 | 670 | 770 | 880 |
| | 850 | 820 | 980 | 810 | 770 | 1040 | 910 | 720 | 740 | 710 | 720 | 680 |
| | 850 | 800 | 900 | 990 | 910 | 980 | 690 | 620 | 730 | 690 | 730 | 590 |
| | 720 | 700 | 1070 | 860 | 1030 | 840 | 530 | 720 | 710 | 760 | 600 | 820 |
| | 850 | 720 | 960 | 900 | 990 | 760 | 780 | 680 | 670 | 700 | 860 | 690 |
| Green Thunder | 560 | 580 | 950 | 700 | 880 | 940 | 730 | 730 | 570 | 570 | 670 | 660 |
| | 500 | 810 | 850 | 800 | 580 | 990 | 730 | 560 | 560 | 750 | 840 | 670 |
| | 580 | 860 | 730 | 780 | 1060 | 750 | 710 | 650 | 790 | 620 | 720 | 730 |
| | 730 | 810 | 950 | 760 | 910 | 940 | 680 | 800 | 740 | 530 | 560 | 660 |
| | 720 | 580 | 900 | 960 | 750 | 750 | 600 | 650 | 530 | 510 | 710 | 630 |
| | 880 | 750 | 710 | 880 | 1040 | 690 | 520 | 630 | 600 | 650 | 700 | 690 |
| | 920 | 580 | 630 | 950 | 850 | 560 | 600 | 570 | 780 | 540 | 560 | 840 |
| | 780 | 680 | 950 | 700 | 890 | 950 | 550 | 630 | 590 | 680 | 860 | 700 |
| | 720 | 750 | 790 | 710 | 1170 | 620 | 700 | 650 | 650 | 640 | 720 | 650 |
| | 940 | 750 | 700 | 750 | 1040 | 1070 | 630 | 600 | 630 | 570 | 630 | 680 |

TABLE 4-continued

| | | | | | | | | | | | | |
|---|---|---|---|---|---|---|---|---|---|---|---|---|
| PIC Cos | 780 | 880 | 530 | 920 | 750 | 880 | 620 | 550 | 620 | 560 | 550 | 860 |
| | 670 | 850 | 810 | 810 | 850 | 630 | 740 | 660 | 620 | 540 | 820 | 710 |
| | 750 | 600 | 600 | 910 | 440 | 790 | 590 | 640 | 650 | 680 | 670 | 660 |
| | 790 | 750 | 860 | 800 | 930 | 450 | 720 | 710 | 570 | 530 | 650 | 690 |
| | 910 | 740 | 760 | 920 | 800 | 1030 | 640 | 630 | 610 | 670 | 580 | 740 |
| | 720 | 830 | 860 | 840 | 870 | 620 | 700 | 660 | 490 | 620 | 610 | 860 |
| | 740 | 870 | 1030 | 670 | 830 | 990 | 540 | 600 | 710 | 690 | 680 | 650 |
| | 730 | 870 | 750 | 850 | 980 | 660 | 600 | 670 | 610 | 650 | 580 | 610 |
| | 600 | 680 | 890 | 730 | 610 | 920 | 610 | 640 | 700 | 570 | 680 | 590 |
| | 690 | 940 | 910 | 800 | 990 | 810 | 530 | 610 | 540 | 600 | 710 | 800 |

Anova: Two-Factor With Replication

| SUMMARY TRUE HEART | | | | | | | | | | | | |
|---|---|---|---|---|---|---|---|---|---|---|---|---|
| Count | 10 | 10 | 10 | 10 | 10 | 10 | 10 | 10 | 10 | 10 | 10 | 10 |
| Sum | 8150.00 | 7870.00 | 8750.00 | 8650.00 | 9630.00 | 9530.00 | 6550.00 | 6880.00 | 7140.00 | 6820.00 | 7360.00 | 7180.00 |
| Average | 815.00 | 787.00 | 875.00 | 865.00 | 963.00 | 953.00 | 655.00 | 688.00 | 714.00 | 682.00 | 736.00 | 718.00 |
| Variance | 5738.89 | 6001.11 | 15250.00 | 5672.22 | 19067.78 | 17734.44 | 15805.56 | 3328.89 | 1382.22 | 3617.78 | 5582.22 | 13506.67 |
| Green Thunder | | | | | | | | | | | | |
| Count | 10 | 10 | 10 | 10 | 10 | 10 | 10 | 10 | 10 | 10 | 10 | 10 |
| Sum | 7330.00 | 7150.00 | 8160.00 | 7990.00 | 9170.00 | 8260.00 | 6450.00 | 6470.00 | 6440.00 | 6060.00 | 6970.00 | 6910.00 |
| Average | 733.00 | 715.00 | 816.00 | 799.00 | 917.00 | 826.00 | 645.00 | 647.00 | 644.00 | 606.00 | 697.00 | 691.00 |
| Variance | 23290.00 | 10961.11 | 14382.22 | 9676.67 | 29201.11 | 30115.56 | 5761.11 | 5178.89 | 8848.89 | 5715.56 | 10112.22 | 3521.11 |
| PIC Cos | | | | | | | | | | | | |
| Count | 10 | 10 | 10 | 10 | 10 | 10 | 10 | 10 | 10 | 10 | 10 | 10 |
| Sum | 7380.00 | 8010.00 | 8000.00 | 8250.00 | 8050.00 | 7780.00 | 6290.00 | 6370.00 | 6120.00 | 6110.00 | 6530.00 | 7170.00 |
| Average | 738.00 | 801.00 | 800.00 | 825.00 | 805.00 | 778.00 | 629.00 | 637.00 | 612.00 | 611.00 | 653.00 | 717.00 |
| Variance | 6728.89 | 11076.67 | 21933.33 | 6738.89 | 29072.22 | 34284.44 | 5143.33 | 1912.22 | 4528.89 | 3565.56 | 6223.33 | 9378.89 |

| TOTALS | TRUE HEART | Green Thunder | PIC COS |
|---|---|---|---|
| Count | 120 | 120 | 120 |
| Sum | 94510.00 | 87360.00 | 86060.00 |
| Average | 787.58 | 728.00 | 717.17 |
| Variance | 18949.57 | 19925.38 | 17188.54 |

ANOVA

| | | | | | | |
|---|---|---|---|---|---|---|
| Variety | 345041.67 | 2 | 172520.83 | 15.15 | 5.146E−07 | 3.02 |
| Locations | 2744694.17 | 11 | 249517.65 | 21.91 | 3.072E−33 | 1.82 |
| Interaction | 236511.67 | 22 | 10750.53 | 0.94 | 0.5367971 | 1.58 |
| Within | 3690350.00 | 324 | 11389.97 | | | |
| Total | 103469.60 | 359 | | | | |

Table 5 below shows the leaf length of True Heart at harvest maturity as compared to Green Thunder and PIC Cos. Leaf width is measured in centimeters. An analysis of variance was performed on the data and is shown below the data. As can be seen from the data in Table 5, True Heart has a significantly longer leaf length than Green Thunder but is significantly smaller than PIC Cos.

TABLE 5

| | Loc. 1 | Loc. 2 | Loc. 3 | Loc. 4 | Loc. 5 | Loc. 6 | Loc. 7 | Loc. 8 | Loc. 9 | Loc. 10 | Loc. 11 | Loc. 12 |
|---|---|---|---|---|---|---|---|---|---|---|---|---|
| | Leaf Length at Maturity (cm) | | | | | | | | | | | |
| Trail Location: | | | | | | | | | | | | |
| TRUE HEART | 26 | 28 | 33 | 33 | 37 | 35 | 33 | 32 | 36 | 37 | 31 | 33 |
| | 31 | 30 | 31 | 29 | 33 | 32 | 34 | 34 | 36 | 36 | 31 | 33 |
| | 29 | 31 | 30 | 27 | 32 | 34 | 34 | 33 | 35 | 35 | 34 | 32 |
| | 30 | 32 | 29 | 28 | 33 | 33 | 33 | 34 | 37 | 37 | 33 | 32 |
| | 28 | 31 | 31 | 30 | 32 | 31 | 32 | 33 | 37 | 36 | 33 | 31 |
| | 29 | 31 | 27 | 30 | 29 | 34 | 35 | 33 | 35 | 37 | 33 | 33 |
| | 28 | 29 | 32 | 29 | 32 | 31 | 32 | 32 | 36 | 35 | 32 | 32 |
| | 29 | 31 | 31 | 29 | 34 | 35 | 31 | 31 | 37 | 36 | 31 | 30 |
| | 29 | 31 | 30 | 29 | 35 | 34 | 35 | 35 | 37 | 36 | 31 | 31 |
| | 30 | 31 | 29 | 31 | 32 | 33 | 33 | 35 | 36 | 37 | 31 | 32 |

TABLE 5-continued

| | | | | | | | | | | | | |
|---|---|---|---|---|---|---|---|---|---|---|---|---|
| Green Thunder | 28 | 25 | 30 | 30 | 33 | 33 | 32 | 33 | 35 | 35 | 30 | 33 |
| | 26 | 26 | 33 | 30 | 32 | 32 | 33 | 33 | 35 | 35 | 33 | 32 |
| | 26 | 26 | 32 | 30 | 31 | 36 | 31 | 31 | 34 | 36 | 32 | 32 |
| | 27 | 24 | 30 | 32 | 32 | 33 | 33 | 33 | 36 | 36 | 31 | 31 |
| | 26 | 28 | 31 | 30 | 35 | 35 | 32 | 33 | 34 | 36 | 32 | 32 |
| | 26 | 27 | 35 | 32 | 33 | 36 | 30 | 32 | 34 | 36 | 32 | 30 |
| | 27 | 29 | 33 | 33 | 34 | 32 | 31 | 34 | 35 | 34 | 32 | 31 |
| | 25 | 29 | 33 | 33 | 30 | 33 | 33 | 33 | 36 | 34 | 31 | 31 |
| | 26 | 26 | 31 | 31 | 34 | 32 | 33 | 32 | 35 | 34 | 32 | 33 |
| | 28 | 29 | 33 | 34 | 35 | 34 | 32 | 32 | 35 | 35 | 33 | 34 |
| PIC Cos | 28 | 30 | 31 | 32 | 34 | 33 | 36 | 36 | 39 | 39 | 35 | 34 |
| | 29 | 30 | 31 | 31 | 36 | 33 | 34 | 34 | 39 | 40 | 32 | 32 |
| | 30 | 28 | 31 | 30 | 32 | 34 | 35 | 33 | 40 | 38 | 35 | 35 |
| | 27 | 29 | 29 | 33 | 30 | 32 | 33 | 35 | 40 | 40 | 35 | 34 |
| | 30 | 28 | 30 | 33 | 36 | 35 | 36 | 34 | 41 | 39 | 31 | 34 |
| | 30 | 28 | 28 | 31 | 34 | 31 | 33 | 34 | 38 | 40 | 33 | 35 |
| | 29 | 35 | 29 | 30 | 31 | 32 | 35 | 35 | 40 | 39 | 35 | 36 |
| | 30 | 29 | 31 | 30 | 33 | 36 | 35 | 36 | 40 | 39 | 38 | 35 |
| | 32 | 28 | 31 | 28 | 33 | 34 | 36 | 33 | 41 | 38 | 34 | 36 |
| | 27 | 30 | 30 | 30 | 33 | 34 | 33 | 33 | 39 | 40 | 36 | 35 |

Anova: Two-Factor With Replication
Leaf length (cm) at Harvest Maturity

| SUMMARY TRUE HEART | | | | | | | | | | | | |
|---|---|---|---|---|---|---|---|---|---|---|---|---|
| Count | 10 | 10 | 10 | 10 | 10 | 10 | 10 | 10 | 10 | 10 | 10 | 10 |
| Sum | 312.00 | 316.00 | 316.00 | 315.00 | 353.00 | 360.00 | 339.00 | 345.00 | 377.00 | 373.00 | 345.00 | 341.00 |
| Average | 31.20 | 31.60 | 31.60 | 31.50 | 35.30 | 36.00 | 33.90 | 34.50 | 37.70 | 37.30 | 34.50 | 34.10 |
| Variance | 2.84 | 2.49 | 2.93 | 2.50 | 5.34 | 2.44 | 0.32 | 0.50 | 0.68 | 0.46 | 1.17 | 0.54 |
| **Green Thunder** | | | | | | | | | | | | |
| Count | 10 | 10 | 10 | 10 | 10 | 10 | 10 | 10 | 10 | 10 | 10 | 10 |
| Sum | 305.00 | 309.00 | 357.00 | 353.00 | 372.00 | 348.00 | 331.00 | 338.00 | 352.00 | 357.00 | 341.00 | 667.00 |
| Average | 30.50 | 30.90 | 35.70 | 35.30 | 37.20 | 34.80 | 33.10 | 33.80 | 35.20 | 35.70 | 34.10 | 66.70 |
| Variance | 2.28 | 0.99 | 4.68 | 4.01 | 4.84 | 4.18 | 0.77 | 0.40 | 3.96 | 1.12 | 0.77 | 10120.01 |
| **PIC Cos** | | | | | | | | | | | | |
| Count | 10 | 10 | 10 | 10 | 10 | 10 | 10 | 10 | 10 | 10 | 10 | 10 |
| Sum | 312.00 | 321.00 | 350.00 | 343.00 | 358.00 | 348.00 | 352.00 | 355.00 | 391.00 | 394.00 | 364.00 | 358.00 |
| Average | 31.20 | 32.10 | 35.00 | 34.30 | 35.80 | 34.80 | 35.20 | 35.50 | 39.10 | 39.40 | 36.40 | 35.80 |
| Variance | 1.73 | 1.66 | 2.22 | 1.12 | 1.73 | 5.96 | 1.73 | 1.39 | 0.77 | 0.49 | 1.16 | 0.84 |

| TOTALS | TRUE HEART | Green Thunder | PIC COS |
|---|---|---|---|
| Count | 120 | 120 | 120 |
| Sum | 3880.00 | 3818.00 | 4030.00 |
| Average | 32.33 | 31.82 | 33.58 |
| Variance | 6.76 | 8.03 | 12.77 |

ANOVA

| Source of Variation | SS | df | MS | F | P-value | F crit |
|---|---|---|---|---|---|---|
| Variety | 477.27 | 2 | 238.63 | 0.84 | 0.43 | 3.02 |
| Locations | 4588.00 | 11 | 417.09 | 1.47 | 0.14 | 1.82 |
| Interaction | 6685.13 | 22 | 303.87 | 1.07 | 0.37 | 1.58 |
| Within | 91719.20 | 324 | 283.08 | | | |
| Total | 103469.60 | 359 | | | | |

Table 6 below shows the leaf index of True Heart at harvest maturity as compared to Green Thunder and PIC Cos. Leaf index is calculated by dividing the leaf length by the leaf width. An analysis of variance was performed on the data and is shown below the data. As can be seen in Table 6, True Heart has a significantly different leaf index than Green Thunder and PIC Cos indicating that True Heart has a different leaf shape than Green Thunder and PIC Cos at harvest maturity.

TABLE 6

| | Loc. 1 | Loc. 2 | Loc. 3 | Loc. 4 | Loc. 5 | Loc. 6 | Loc. 7 | Loc. 8 | Loc. 9 | Loc. 10 | Loc. 11 | Loc. 12 |
|---|---|---|---|---|---|---|---|---|---|---|---|---|
| | | | | | | Leaf index at Harvest Maturity | | | | | | |
| Trail Location: | | | | | | | | | | | | |
| TRUE | 1.53 | 1.56 | 1.57 | 1.50 | 1.48 | 1.52 | 1.74 | 1.68 | 2.25 | 2.06 | 1.63 | 1.57 |
| HEART | 1.48 | 1.58 | 1.55 | 1.71 | 1.50 | 1.45 | 1.79 | 1.79 | 2.12 | 2.12 | 1.55 | 1.57 |
| | 1.45 | 1.72 | 1.36 | 1.23 | 1.28 | 1.31 | 1.70 | 1.74 | 1.94 | 2.19 | 1.79 | 1.45 |
| | 1.58 | 1.60 | 1.38 | 1.27 | 1.27 | 1.43 | 1.74 | 1.70 | 2.18 | 2.06 | 1.65 | 1.68 |
| | 1.75 | 1.63 | 1.55 | 1.50 | 1.45 | 1.55 | 1.68 | 1.74 | 2.06 | 2.12 | 1.83 | 1.55 |
| | 1.71 | 1.63 | 1.42 | 1.58 | 1.38 | 1.31 | 1.75 | 1.83 | 2.19 | 2.18 | 1.74 | 1.57 |
| | 1.56 | 1.71 | 1.33 | 1.38 | 1.39 | 1.55 | 1.78 | 1.78 | 2.00 | 2.19 | 1.52 | 1.78 |
| | 1.61 | 1.48 | 1.48 | 1.38 | 1.31 | 1.52 | 1.72 | 1.72 | 2.18 | 2.00 | 1.63 | 1.50 |
| | 1.61 | 1.55 | 1.25 | 1.38 | 1.40 | 1.55 | 1.75 | 1.75 | 2.18 | 2.00 | 1.55 | 1.63 |
| | 1.76 | 1.55 | 1.32 | 1.41 | 1.39 | 1.32 | 1.83 | 1.75 | 2.00 | 2.18 | 1.63 | 1.60 |
| Green | 1.47 | 1.47 | 1.43 | 1.20 | 1.32 | 1.18 | 1.60 | 1.83 | 2.06 | 1.94 | 1.50 | 1.57 |
| Thunder | 1.37 | 1.53 | 1.38 | 1.43 | 1.68 | 1.52 | 1.83 | 1.65 | 1.94 | 2.06 | 1.65 | 1.68 |
| | 1.44 | 1.53 | 1.52 | 1.43 | 1.24 | 1.44 | 1.72 | 1.72 | 2.00 | 2.12 | 1.45 | 1.60 |
| | 1.59 | 1.41 | 1.25 | 1.39 | 1.33 | 1.32 | 1.57 | 1.65 | 2.00 | 2.12 | 1.72 | 1.55 |
| | 1.63 | 1.47 | 1.48 | 1.50 | 1.40 | 1.46 | 1.68 | 1.74 | 2.00 | 2.00 | 1.52 | 1.68 |
| | 1.63 | 1.69 | 1.52 | 1.39 | 1.27 | 1.50 | 1.50 | 1.60 | 1.89 | 2.12 | 1.78 | 1.43 |
| | 1.59 | 1.71 | 1.50 | 1.74 | 1.62 | 1.33 | 1.63 | 1.79 | 1.94 | 2.00 | 1.78 | 1.82 |
| | 1.39 | 1.81 | 1.50 | 1.50 | 1.50 | 1.32 | 1.74 | 1.65 | 2.12 | 1.89 | 1.72 | 1.55 |
| | 1.44 | 1.53 | 1.55 | 1.24 | 1.36 | 1.88 | 1.65 | 1.68 | 2.06 | 2.00 | 1.52 | 1.74 |
| | 1.56 | 1.61 | 1.43 | 1.70 | 1.52 | 1.21 | 1.68 | 1.78 | 1.94 | 1.94 | 1.50 | 1.70 |
| PIC Cos | 1.47 | 1.76 | 1.41 | 1.60 | 1.55 | 1.57 | 1.89 | 2.00 | 1.95 | 2.29 | 1.67 | 1.36 |
| | 1.45 | 1.58 | 1.35 | 1.19 | 1.64 | 1.43 | 1.62 | 1.70 | 2.29 | 2.35 | 1.52 | 1.52 |
| | 1.67 | 1.56 | 1.48 | 1.50 | 1.33 | 1.70 | 2.06 | 1.83 | 2.50 | 2.11 | 1.67 | 1.75 |
| | 1.50 | 1.53 | 1.26 | 1.57 | 1.50 | 1.45 | 1.57 | 1.84 | 2.22 | 2.50 | 1.84 | 1.79 |
| | 1.50 | 1.56 | 1.50 | 1.57 | 1.71 | 1.52 | 2.12 | 1.79 | 2.41 | 2.17 | 1.55 | 1.70 |
| | 1.67 | 1.65 | 1.33 | 1.41 | 1.55 | 1.24 | 1.65 | 1.62 | 2.00 | 2.11 | 1.74 | 1.67 |
| | 1.53 | 1.59 | 1.61 | 1.50 | 1.63 | 1.39 | 1.84 | 1.84 | 2.35 | 2.17 | 1.67 | 1.80 |
| | 1.50 | 1.45 | 1.48 | 1.67 | 1.38 | 1.38 | 1.67 | 1.89 | 2.11 | 2.05 | 1.73 | 1.84 |
| | 1.68 | 1.56 | 1.55 | 1.40 | 1.50 | 1.48 | 2.00 | 1.65 | 2.41 | 2.38 | 1.48 | 1.80 |
| | 1.50 | 1.50 | 1.43 | 1.43 | 1.38 | 1.42 | 1.65 | 1.74 | 1.95 | 2.00 | 1.64 | 1.84 |
| | | | | | | Anova: Two-Factor With Replication<br>Leaf Index (calculated by dividing the leaf length by the leaf width) | | | | | | |
| SUMMARY TRUE HEART | | | | | | | | | | | | |
| Count | 10 | 10 | 10 | 10 | 10 | 10 | 10 | 10 | 10 | 10 | 10 | 10.00 |
| Sum | 16.03 | 16.00 | 14.21 | 14.34 | 13.86 | 14.51 | 17.48 | 17.48 | 21.08 | 21.07 | 16.53 | 15.91 |
| Average | 1.60 | 1.60 | 1.42 | 1.43 | 1.39 | 1.45 | 1.75 | 1.75 | 2.11 | 2.11 | 1.65 | 1.59 |
| Variance | 0.01 | 0.01 | 0.01 | 0.02 | 0.01 | 0.01 | 0.00 | 0.00 | 0.01 | 0.01 | 0.01 | 0.01 |
| Green Thunder | | | | | | | | | | | | |
| Count | 10 | 10 | 10 | 10 | 10 | 10 | 10 | 10 | 10 | 10 | 10 | 10.00 |
| Sum | 15.10 | 15.76 | 14.56 | 14.52 | 14.25 | 14.17 | 16.61 | 17.09 | 19.96 | 20.19 | 16.15 | 16.33 |
| Average | 1.51 | 1.58 | 1.46 | 1.45 | 1.42 | 1.42 | 1.66 | 1.71 | 2.00 | 2.02 | 1.62 | 1.63 |
| Variance | 0.01 | 0.02 | 0.01 | 0.03 | 0.02 | 0.04 | 0.01 | 0.01 | 0.00 | 0.01 | 0.02 | 0.01 |
| PIC Cos | | | | | | | | | | | | |
| Count | 10 | 10 | 10 | 10 | 10 | 10 | 10 | 10 | 10 | 10 | 10 | 10.00 |
| Sum | 15.47 | 15.72 | 14.39 | 14.84 | 15.16 | 14.59 | 18.07 | 17.91 | 22.20 | 22.12 | 16.49 | 17.07 |
| Average | 1.55 | 1.57 | 1.44 | 1.48 | 1.52 | 1.46 | 1.81 | 1.79 | 2.22 | 2.21 | 1.65 | 1.71 |
| Variance | 0.01 | 0.01 | 0.01 | 0.02 | 0.02 | 0.02 | 0.04 | 0.01 | 0.04 | 0.03 | 0.01 | 0.02 |

| TOTALS | TRUE HEART | Green Thunder | PIC COS |
|---|---|---|---|
| Count | 120 | 120 | 120 |
| Sum | 198.52 | 194.69 | 204.04 |
| Average | 1.65 | 1.62 | 1.70 |
| Variance | 0.06 | 0.05 | 0.09 |

TABLE 6-continued

| ANOVA | | | | | | |
|---|---|---|---|---|---|---|
| Source of Variation | SS | df | MS | F | P-value | F crit |
| Variety | 0.37 | 2 | 0.18 | 12.74 | 4.739E−06 | 3.02 |
| Locations | 18.70 | 11 | 1.70 | 117.53 | 5.32E-106 | 1.82 |
| Interaction | 0.46 | 22 | 0.02 | 1.43 | 0.0966146 | 1.58 |
| Within | 4.69 | 324 | 0.01 | | | |
| Total | 24.20 | 359 | | | | |

Table 7 below shows the leaf area of True Heart at harvest maturity as compared to Green Thunder and PIC Cos. Leaf area is calculated by multiplying the leaf length by the leaf width. An analysis of variance was performed on the data and is shown below the data. As can be seen in Table 7, True Heart has a significantly larger leaf area than Green Thunder but a smaller leaf area than PIC Cos at harvest maturity.

TABLE 7

| | Loc. 1 | | Loc. 2 | Loc. 3 | Loc. 4 | Loc. 5 | Loc. 6 | Loc. 7 | Loc. 8 | Loc. 9 | Loc. 10 | Loc. 11 | Loc. 12 |
|---|---|---|---|---|---|---|---|---|---|---|---|---|---|
| Leaf Area at Harvest Maturity | | | | | | | | | | | | | |
| Trail Location: | | | | | | | | | | | | | |
| TRUE | 442 | | 504 | 693 | 726 | 925 | 805 | 627 | 608 | 576 | 666 | 589 | 693 |
| HEART | 651 | | 570 | 620 | 493 | 726 | 704 | 646 | 646 | 612 | 612 | 620 | 693 |
| | 580 | 558 | 660 | 594 | 800 | 884 | 680 | 627 | 630 | 560 | 646 | 704 | |
| | 570 | | 640 | 609 | 616 | 858 | 759 | 627 | 680 | 629 | 666 | 660 | 608 |
| | 448 | | 589 | 620 | 600 | 704 | 620 | 608 | 627 | 666 | 612 | 594 | 620 |
| | 493 | | 589 | 513 | 570 | 609 | 884 | 700 | 594 | 560 | 629 | 627 | 693 |
| | 504 | | 493 | 768 | 609 | 736 | 620 | 576 | 576 | 648 | 560 | 672 | 576 |
| | 522 | | 651 | 651 | 609 | 884 | 805 | 558 | 558 | 629 | 648 | 589 | 600 |
| | 522 | | 620 | 720 | 609 | 875 | 748 | 700 | 700 | 629 | 648 | 620 | 589 |
| | 510 | | 620 | 638 | 682 | 736 | 825 | 594 | 700 | 648 | 629 | 589 | 640 |
| Green | 532 | | 425 | 630 | 750 | 825 | 924 | 640 | 594 | 595 | 630 | 600 | 693 |
| Thunder | 494 | | 442 | 792 | 630 | 608 | 672 | 594 | 660 | 630 | 595 | 660 | 608 |
| | 468 | | 442 | 672 | 630 | 775 | 900 | 558 | 558 | 578 | 612 | 704 | 640 |
| | 459 | | 408 | 720 | 736 | 768 | 825 | 693 | 660 | 648 | 612 | 558 | 620 |
| | 416 | | 532 | 651 | 600 | 875 | 840 | 608 | 627 | 578 | 648 | 672 | 608 |
| | 416 | | 432 | 805 | 736 | 858 | 864 | 600 | 640 | 612 | 612 | 576 | 630 |
| | 459 | | 493 | 726 | 627 | 714 | 768 | 589 | 646 | 630 | 578 | 576 | 527 |
| | 450 | | 464 | 726 | 726 | 600 | 825 | 627 | 660 | 612 | 612 | 558 | 620 |
| | 468 | | 442 | 620 | 775 | 850 | 544 | 660 | 608 | 595 | 578 | 672 | 627 |
| | 504 | | 522 | 759 | 680 | 805 | 952 | 608 | 576 | 630 | 630 | 726 | 680 |
| PIC Cos | 532 | | 510 | 682 | 640 | 748 | 693 | 684 | 648 | 780 | 663 | 735 | 850 |
| | 580 | | 570 | 713 | 806 | 792 | 759 | 714 | 680 | 663 | 680 | 672 | 672 |
| | 540 | | 504 | 651 | 600 | 768 | 680 | 595 | 594 | 640 | 684 | 735 | 700 |
| | 486 | | 551 | 667 | 693 | 600 | 704 | 693 | 665 | 720 | 640 | 665 | 646 |
| | 600 | | 504 | 600 | 693 | 756 | 805 | 612 | 646 | 697 | 702 | 620 | 680 |
| | 540 | | 476 | 588 | 682 | 748 | 775 | 660 | 714 | 722 | 760 | 627 | 735 |
| | 551 | | 770 | 522 | 600 | 589 | 736 | 665 | 665 | 680 | 702 | 735 | 720 |
| | 600 | | 580 | 651 | 540 | 792 | 936 | 735 | 684 | 760 | 741 | 836 | 665 |
| | 608 | 504 | 620 | 560 | 726 | 782 | 648 | 660 | 697 | 608 | 782 | 720 | |
| | 486 | | 600 | 630 | 630 | 792 | 816 | 660 | 627 | 780 | 800 | 792 | 665 |

Anova: Two-Factor With Replication
Leaf Area (cm2, calculated by multiplying the leaf length by the leaf width)

| SUMMARY | Loc. 1 | Loc. 2 | Loc. 3 | Loc. 4 | Loc. 5 | Loc. 6 | Loc. 7 | Loc. 8 | Loc. 9 | Loc. 10 | Loc. 11 | Loc. 12 |
|---|---|---|---|---|---|---|---|---|---|---|---|---|
| TRUE HEART | | | | | | | | | | | | |
| Count | 10 | 10 | 10 | 10 | 10 | 10 | 10 | 10 | 10 | 10 | 10 | 10 |
| Sum | 5242.00 | 5834.00 | 6492.00 | 6108.00 | 7853.00 | 7654.00 | 6316.00 | 6316.00 | 6227.00 | 6230.00 | 6206.00 | 6416.00 |
| Average | 524.20 | 583.40 | 649.20 | 610.80 | 785.30 | 765.40 | 631.60 | 631.60 | 622.70 | 623.00 | 620.60 | 641.60 |
| Variance | 3938.40 | 2868.49 | 4795.73 | 3813.07 | 9874.90 | 9024.04 | 2492.04 | 2492.04 | 1061.57 | 1466.67 | 953.82 | 2468.71 |
| Green Thunder | | | | | | | | | | | | |
| Count | 10 | 10 | 10 | 10 | 10 | 10 | 10 | 10 | 10 | 10 | 10 | 10 |
| Sum | 4666.00 | 4602.00 | 7101.00 | 6890.00 | 7678.00 | 8114.00 | 6177.00 | 6229.00 | 6108.00 | 6107.00 | 6302.00 | 6253.00 |
| Average | 466.60 | 460.20 | 710.10 | 689.00 | 767.80 | 811.40 | 617.70 | 622.90 | 610.80 | 610.70 | 630.20 | 625.30 |
| Variance | 1326.93 | 1757.51 | 4242.99 | 3968.00 | 9742.18 | 15230.04 | 1499.34 | 1382.32 | 571.51 | 503.12 | 4024.40 | 2014.90 |

TABLE 7-continued

| PIC Cos | | | | | | | | | | | | |
|---|---|---|---|---|---|---|---|---|---|---|---|---|
| Count | 10 | 10 | 10 | 10 | 10 | 10 | 10 | 10 | 10 | 10 | 10 | 10 |
| Sum | 5523.00 | 5569.00 | 6324.00 | 6444.00 | 7311.00 | 7686.00 | 6666.00 | 6583.00 | 7139.00 | 6980.00 | 7199.00 | 7053.00 |
| Average | 552.30 | 556.90 | 632.40 | 644.40 | 731.10 | 768.60 | 666.60 | 658.30 | 713.90 | 698.00 | 719.90 | 705.30 |
| Variance | 1992.01 | 7238.77 | 2912.71 | 6049.38 | 5676.10 | 5634.27 | 1829.82 | 1077.57 | 2304.32 | 3259.78 | 5237.43 | 3421.57 |

| TOTALS | TRUE HEART | Green Thunder | PIC COS |
|---|---|---|---|
| Count | 120 | 120 | 120 |
| Sum | 76894.0 | 76227.0 | 80477.00 |
| Average | 640.78 | 635.23 | 670.64 |
| Variance | 8085.15 | 13411.57 | 7624.40 |

ANOVA

| Source of Variation | SS | df | MS | F | P-value | F crit |
|---|---|---|---|---|---|---|
| Variety | 87070.22 | 2.00 | 43535.11 | 11.34 | 1.729E−05 | 3.02 |
| Locations | 1870653.83 | 11.00 | 170059.44 | 44.32 | 4.723E−58 | 1.82 |
| Interaction | 351440.85 | 22.00 | 15974.58 | 4.16 | 5.012E−09 | 1.58 |
| Within | 1243318.20 | 324.00 | 3837.40 | | | |
| Total | 3552483.10 | 359.00 | | | | |

Table 8 below shows the core diameter of True Heart at harvest maturity as compared to Green Thunder and PIC Cos. Core length is measured in centimeters. An analysis of variance was performed on the data and is shown below the data. As can be seen in Table 8, True Heart has a significantly smaller core diameter than PIC Cos at harvest maturity.

TABLE 8

| | Loc. 1 | Loc. 2 | Loc. 3 | Loc. 4 | Loc. 5 | Loc. 6 | Loc. 7 | Loc. 8 | Loc. 9 | Loc. 10 | Loc. 11 | Loc. 12 |
|---|---|---|---|---|---|---|---|---|---|---|---|---|
| | Core Diameter at Harvest Maturity | | | | | | | | | | | |
| Trail Location: | | | | | | | | | | | | |
| TRUE HEART | 4.0 | 4.0 | 4.0 | 4.5 | 4.0 | 3.5 | 3.4 | 3.6 | 3.2 | 3.8 | 3.8 | 3.6 |
| | 4.0 | 4.0 | 4.0 | 4.0 | 4.4 | 4.0 | 3.2 | 3.4 | 3.5 | 3.7 | 4.0 | 3.7 |
| | 4.0 | 4.0 | 4.0 | 4.0 | 4.9 | 4.2 | 4.0 | 3.2 | 3.8 | 3.6 | 3.1 | 3.7 |
| | 3.5 | 3.5 | 4.0 | 4.5 | 4.2 | 3.8 | 3.4 | 3.7 | 3.5 | 3.5 | 3.7 | 3.7 |
| | 4.0 | 4.0 | 4.0 | 3.5 | 4.0 | 4.2 | 3.6 | 4.1 | 3.5 | 3.2 | 3.7 | 3.8 |
| | 4.0 | 3.5 | 3.5 | 4.0 | 4.0 | 4.0 | 3.8 | 3.2 | 3.3 | 3.2 | 3.5 | 3.8 |
| | 3.5 | 3.5 | 4.5 | 3.0 | 3.5 | 3.3 | 3.6 | 3.4 | 3.6 | 3.6 | 3.1 | 3.4 |
| | 3.5 | 4.0 | 4.5 | 4.5 | 4.8 | 4.0 | 3.9 | 3.9 | 3.6 | 3.5 | 3.6 | 3.8 |
| | 4.0 | 4.0 | 4.0 | 4.5 | 4.0 | 3.5 | 3.2 | 3.6 | 3.8 | 3.5 | 3.6 | 3.7 |
| | 4.0 | 4.0 | 3.5 | 4.0 | 3.7 | 4.2 | 3.7 | 4.1 | 3.5 | 3.2 | 3.8 | 3.6 |
| Green Thunder | 4.0 | 3.5 | 4.5 | 4.0 | 4.2 | 4.6 | 3.5 | 3.3 | 3.7 | 3.6 | 3.7 | 3.5 |
| | 4.0 | 4.0 | 4.5 | 4.0 | 3.5 | 3.4 | 3.8 | 3.7 | 3.5 | 3.5 | 3.8 | 3.8 |
| | 4.0 | 4.0 | 3.5 | 3.5 | 4.2 | 4.0 | 3.2 | 3.8 | 3.5 | 3.7 | 3.8 | 3.8 |
| | 3.0 | 4.0 | 4.0 | 3.5 | 4.5 | 4.5 | 3.5 | 3.6 | 3.8 | 3.8 | 3.5 | 3.5 |
| | 3.5 | 4.0 | 4.0 | 3.5 | 4.0 | 4.5 | 3.8 | 3.8 | 3.6 | 3.8 | 3.5 | 3.6 |
| | 3.5 | 3.5 | 3.5 | 3.5 | 4.0 | 4.0 | 3.5 | 3.8 | 3.5 | 3.7 | 3.5 | 3.8 |
| | 3.5 | 4.0 | 4.0 | 4.0 | 4.0 | 3.8 | 3.2 | 3.6 | 3.8 | 3.6 | 3.8 | 3.8 |
| | 4.0 | 3.5 | 3.5 | 4.0 | 4.1 | 4.0 | 3.8 | 3.5 | 3.5 | 3.6 | 3.4 | 3.9 |
| | 3.5 | 4.0 | 3.5 | 4.0 | 3.3 | 4.2 | 3.6 | 3.7 | 3.8 | 3.5 | 3.5 | 3.7 |
| | 3.5 | 4.0 | 3.5 | 3.5 | 3.9 | 3.6 | 3.6 | 3.7 | 3.7 | 3.5 | 3.2 | 3.7 |
| PIC Cos | 4.0 | 4.5 | 4.0 | 4.0 | 4.2 | 4.0 | 4.0 | 4.0 | 3.5 | 4.0 | 4.0 | 3.9 |
| | 4.0 | 5.0 | 4.0 | 3.5 | 3.7 | 3.4 | 4.2 | 4.8 | 4.0 | 3.9 | 3.5 | 4.1 |
| | 5.0 | 5.0 | 4.0 | 4.0 | 4.0 | 2.7 | 4.0 | 3.8 | 3.8 | 4.0 | 4.1 | 3.6 |
| | 5.0 | 5.0 | 4.0 | 4.0 | 4.2 | 3.0 | 4.8 | 4.0 | 4.0 | 3.9 | 4.1 | 3.1 |
| | 5.0 | 5.0 | 4.0 | 4.0 | 4.2 | 4.0 | 4.0 | 4.2 | 4.0 | 3.7 | 3.6 | 4.0 |
| | 5.5 | 5.0 | 4.0 | 4.5 | 3.5 | 3.2 | 4.2 | 4.7 | 3.9 | 4.0 | 3.8 | 3.9 |
| | 5.0 | 5.0 | 4.0 | 4.0 | 3.6 | 3.7 | 3.8 | 4.2 | 3.5 | 3.8 | 4.0 | 3.8 |
| | 5.5 | 5.0 | 4.0 | 4.5 | 4.7 | 3.3 | 4.4 | 4.0 | 4.0 | 3.6 | 3.6 | 4.0 |
| | 5.0 | 5.0 | 4.0 | 4.0 | 4.0 | 3.6 | 4.2 | 4.8 | 3.7 | 4.0 | 3.9 | 3.9 |
| | 5.0 | 4.5 | 4.0 | 3.5 | 4.0 | 3.0 | 4.2 | 4.2 | 3.7 | 3.8 | 3.9 | 3.9 |

TABLE 8-continued

Anova: Two-Factor With Replication
Core Diameter cm at Harvest Maturity

| SUMMARY | | | | | | | | | | | | |
|---|---|---|---|---|---|---|---|---|---|---|---|---|
| TRUE HEART | | | | | | | | | | | | |
| Count | 10 | 10 | 10 | 10 | 10 | 10 | 10 | 10 | 10 | 10 | 10 | 10 |
| Sum | 38.50 | 38.50 | 40.00 | 40.50 | 41.50 | 38.70 | 35.80 | 36.20 | 35.30 | 34.80 | 35.90 | 36.80 |
| Average | 3.85 | 3.85 | 4.00 | 4.05 | 4.15 | 3.87 | 3.58 | 3.62 | 3.53 | 3.48 | 3.59 | 3.68 |
| Variance | 0.06 | 0.06 | 0.11 | 0.25 | 0.20 | 0.11 | 0.08 | 0.11 | 0.04 | 0.05 | 0.09 | 0.02 |
| Green Thunder | | | | | | | | | | | | |
| Count | 10 | 10 | 10 | 10 | 10 | 10 | 10 | 10 | 10 | 10 | 10 | 10 |
| Sum | 36.50 | 38.50 | 38.50 | 37.50 | 39.70 | 40.60 | 35.50 | 36.50 | 36.40 | 36.30 | 35.70 | 37.10 |
| Average | 3.65 | 3.85 | 3.85 | 3.75 | 3.97 | 4.06 | 3.55 | 3.65 | 3.64 | 3.63 | 3.57 | 3.71 |
| Variance | 0.11 | 0.06 | 0.17 | 0.07 | 0.12 | 0.16 | 0.05 | 0.02 | 0.02 | 0.01 | 0.04 | 0.02 |
| PIC Cos | | | | | | | | | | | | |
| Count | 10 | 10 | 10 | 10 | 10 | 10 | 10 | 10 | 10 | 10 | 10 | 10 |
| Sum | 49.00 | 49.00 | 40.00 | 40.00 | 40.10 | 33.90 | 41.80 | 42.70 | 38.10 | 38.70 | 38.50 | 38.20 |
| Average | 4.90 | 4.90 | 4.00 | 4.00 | 4.01 | 3.39 | 4.18 | 4.27 | 3.81 | 3.87 | 3.85 | 3.82 |
| Variance | 0.27 | 0.04 | 0.00 | 0.11 | 0.12 | 0.19 | 0.08 | 0.13 | 0.04 | 0.02 | 0.05 | 0.08 |

| TOTALS | TRUE HEART | Green Thunder | PIC COS |
|---|---|---|---|
| Count | 120 | 120 | 120 |
| Sum | 452.50 | 448.80 | 490.00 |
| Average | 3.77 | 3.74 | 4.08 |
| Variance | 0.13 | 0.09 | 0.26 |

ANOVA

| Source of Variation | SS | df | MS | F | P-value | F crit |
|---|---|---|---|---|---|---|
| Variety | 0.56 | 2.00 | 0.28 | 0.43 | 0.6504778 | 3.02 |
| Locations | 134.60 | 11.00 | 12.24 | 18.87 | 4.048E−29 | 1.82 |
| Interaction | 62.69 | 22.00 | 2.85 | 4.39 | 1.049E−09 | 1.58 |
| Within | 210.11 | 324.00 | 0.65 | | | |
| Total | 407.95 | 359.00 | | | | |

Table 9 below shows the length of the fourth true leaf of True Heart as compared to Green Thunder and PIC Cos. Leaf length is measured in centimeters of a 20-day old seedling. An analysis of variance was performed on the data and is shown below the data. As can be seen in Table 9, True Heart has a significantly longer fourth leaf length than Green Thunder and PIC Cos.

TABLE 9

4th Leaf Length (cm)

| True Heart | Green Thunder | PIC COS |
|---|---|---|
| 7.5 | 3.8 | 3.8 |
| 7.4 | 4.3 | 3.9 |
| 7.6 | 3.9 | 3.6 |
| 7.0 | 4.1 | 4.2 |
| 7.8 | 3.9 | 3.7 |
| 7.5 | 4.4 | 3.8 |
| 8.0 | 4.6 | 3.9 |
| 6.2 | 3.5 | 4.0 |
| 8.0 | 4.1 | 4.1 |
| 5.4 | 4.3 | 4.0 |
| 6.5 | 3.8 | 3.9 |
| 6.5 | 4.0 | 3.9 |
| 6.5 | 4.1 | 4.0 |

TABLE 9-continued

| | | |
|---|---|---|
| 5.2 | 4.2 | 4.1 |
| 4.4 | 4.0 | 4.5 |

Anova: Single Factor
SUMMARY

| Groups | Count | Sum | Average | Variance |
|---|---|---|---|---|
| TRUE HEART | 15 | 101.500 | 6.767 | 1.200 |
| Green Thunder | 15 | 61.000 | 4.067 | 0.075 |
| PIC Cos | 15 | 59.400 | 3.960 | 0.047 |

ANOVA

| Source of Variation | SS | Df | MS | F | P-value | F crit |
|---|---|---|---|---|---|---|
| Between Varieties | 75.894 | 2 | 37.947 | 86.137 | 0.0000 | 3.220 |
| Within Varieties | 18.503 | 42 | 0.441 | | | |
| Total | 94.396 | 44 | | | | |

Table 10 below shows the width of the fourth true leaf of True Heart as compared to Green Thunder and PIC Cos. Leaf width is measured in centimeters of a 20-day old seedling. An analysis of variance was performed on the data and is shown below the data. As can be seen in Table 10, True Heart has a significantly wider fourth leaf width than Green Thunder and PIC Cos.

TABLE 10

| 4th Leaf Width (cm) | | |
| --- | --- | --- |
| True Heart | Green Thunder | PIC Cos |
| 3.2 | 2.6 | 2.3 |
| 3.0 | 2.8 | 2.5 |
| 3.4 | 2.5 | 2.2 |
| 3.3 | 2.6 | 2.5 |
| 3.5 | 2.4 | 2.1 |
| 3.4 | 2.5 | 2.4 |
| 3.5 | 2.6 | 2.3 |
| 2.8 | 2.2 | 2.5 |
| 4.0 | 2.6 | 2.5 |
| 2.5 | 2.8 | 2.4 |
| 2.8 | 2.6 | 2.4 |
| 2.8 | 2.5 | 2.2 |
| 2.8 | 2.5 | 2.4 |
| 2.5 | 2.7 | 2.5 |
| 2.0 | 2.8 | 2.6 |

Anova: Single Factor
SUMMARY

| Groups | Count | Sum | Average | Variance |
| --- | --- | --- | --- | --- |
| TRUE HEART | 16 | 48.300 | 3.019 | 0.243 |
| Green Thunder | 16 | 41.700 | 2.606 | 0.035 |
| PIC Cos | 16 | 39.300 | 2.456 | 0.096 |

ANOVA

| Source of Variation | SS | df | MS | F | P-value | F crit |
| --- | --- | --- | --- | --- | --- | --- |
| Between Varieties | 2.715 | 2 | 1.358 | 10.883 | 0.000 | 3.204 |
| Within Varieties | 5.613 | 45 | 0.125 | | | |
| Total | 8.328 | 47 | | | | |

Table 11 below shows the leaf index of the fourth true leaf of True Heart as compared to Green Thunder and PIC Cos. Leaf index is calculated by dividing the leaf length by the leaf width of the fourth true leaf of a 20-day old seedling. An analysis of variance was performed on the data and is shown below the data. As can be seen in Table 11, True Heart has a significantly different leaf index than both Green Thunder and PIC Cos indicating that True Heart has a different fourth true leaf shape than either Green Thunder or PIC Cos.

TABLE 11

| 4th Leaf Index | | |
| --- | --- | --- |
| True Heart | Green Thunder | PIC Cos |
| 2.3 | 1.5 | 1.7 |
| 2.5 | 1.5 | 1.6 |
| 2.2 | 1.6 | 1.6 |
| 2.1 | 1.6 | 1.7 |
| 2.2 | 1.6 | 1.8 |
| 2.2 | 1.8 | 1.6 |
| 2.3 | 1.8 | 1.7 |
| 2.2 | 1.6 | 1.6 |
| 2.0 | 1.6 | 1.6 |
| 2.2 | 1.5 | 1.7 |
| 2.3 | 1.5 | 1.6 |
| 2.3 | 1.6 | 1.8 |
| 2.3 | 1.6 | 1.7 |
| 2.1 | 1.6 | 1.6 |
| 2.2 | 1.4 | 1.7 |

TABLE 11-continued

Anova: Single Factor
SUMMARY

| Groups | Count | Sum | Average | Variance |
| --- | --- | --- | --- | --- |
| True Heart | 15 | 33.506 | 2.234 | 0.014 |
| Green Thunder | 15 | 23.678 | 1.579 | 0.009 |
| PIC Cos | 15 | 24.911 | 1.661 | 0.004 |

ANOVA

| Source of Variation | SS | df | MS | F | P-value | F crit |
| --- | --- | --- | --- | --- | --- | --- |
| Between Groups | 3.822 | 2 | 1.911 | 215.135 | 0.000 | 3.220 |
| Within Groups | 0.373 | 42 | 0.009 | | | |
| Total | 4.194739 | 44 | | | | |

Table 12 below shows the cotyledon length of True Heart as compared to Green Thunder and PIC Cos. Cotyledon length was measured in millimeters. An analysis of variance was performed on the data and is shown below the data. As can be seen in Table 12, True Heart has a significantly longer cotyledon length than Green Thunder and PIC Cos.

TABLE 12

| Cotyledon length (mm) | | |
| --- | --- | --- |
| True Heart | Green Thunder | PIC Cos |
| 20 | 15 | 14 |
| 16 | 15 | 14 |
| 20 | 15 | 14 |
| 18 | 16 | 12 |
| 19 | 16 | 14 |
| 22 | 15 | 14 |
| 18 | 13 | 14 |
| 22 | 13 | 16 |
| 19 | 15 | 16 |
| 20 | 15 | 16 |
| 20 | 15 | 14 |
| 18 | 15 | 14 |

Anova: Single Factor
SUMMARY

| Groups | Count | Sum | Average | Variance |
| --- | --- | --- | --- | --- |
| True Heart | 12 | 232 | 19.3333 | 2.969697 |
| Green Thunder | 12 | 178 | 14.8333 | 0.878788 |
| PIC Cos | 12 | 172 | 14.3333 | 1.333333 |

ANOVA

| Source of Variation | SS | df | MS | F | P-value | F crit |
| --- | --- | --- | --- | --- | --- | --- |
| Between Groups | 182 | 2 | 91 | 52.68421 | 5.35E−11 | 3.284924 |
| Within Groups | 57 | 33 | 1.72727 | | | |
| Total | 239 | 35 | | | | |

Table 13 below shows the cotyledon width of True Heart as compared to Green Thunder and PIC Cos. Cotyledon width was measured in millimeters. An analysis of variance was performed on the data and is shown below the data. As can be seen in Table 13, True Heart has a significantly wider cotyledon width PIC Cos.

TABLE 13

| Cotyledon Width (mm) | | |
|---|---|---|
| True Heart | Green Thunder | PIC Cos |
| 10 | 10 | 9 |
| 9 | 10 | 8 |
| 10 | 10 | 9 |
| 10 | 10 | 8 |
| 9 | 10 | 8 |
| 11 | 11 | 8 |
| 9 | 9 | 8 |
| 11 | 9 | 8 |
| 9 | 10 | 9 |
| 11 | 10 | 9 |
| 10 | 10 | 8 |
| 10 | 10 | 8 |

Anova: Single Factor
SUMMARY

| Groups | Count | Sum | Average | Variance |
|---|---|---|---|---|
| True Heart | 12 | 119 | 9.91667 | 0.628788 |
| Green Thunder | 12 | 119 | 9.91667 | 0.265152 |
| PIC Cos | 12 | 100 | 8.33333 | 0.242424 |

ANOVA

| Source of Variation | SS | df | MS | F | P-value | F crit |
|---|---|---|---|---|---|---|
| Between Groups | 20.055556 | 2 | 10.0278 | 26.47333 | 1.38E−07 | 3.284924 |
| Within Groups | 12.5 | 33 | 0.37879 | | | |
| Total | 32.555556 | 35 | | | | |

Table 14 below shows the cotyledon index of True Heart as compared to Green Thunder and PIC Cos. Cotyledon index is calculated by dividing the cotyledon leaf length by the cotyledon leaf width. An analysis of variance was performed on the data and is shown below the data. As can be seen in Table 14, True Heart has a significantly different cotyledon index than both Green Thunder and PIC Cos indicating that True Heart has a different cotyledon leaf shape than both Green Thunder and PIC Cos.

TABLE 14

| Cotyledon Index (mm) | | |
|---|---|---|
| True Heart | Green Thunder | PIC Cos |
| 2.0 | 1.5 | 1.6 |
| 1.8 | 1.5 | 1.8 |
| 2.0 | 1.5 | 1.6 |
| 1.8 | 1.6 | 1.5 |
| 2.1 | 1.6 | 1.8 |
| 2.0 | 1.4 | 1.8 |
| 2.0 | 1.4 | 1.8 |
| 2.0 | 1.4 | 2.0 |
| 2.1 | 1.5 | 1.8 |
| 1.8 | 1.5 | 1.8 |
| 2.0 | 1.5 | 1.8 |
| 1.8 | 1.5 | 1.8 |

TABLE 14-continued

Anova: Single Factor
SUMMARY

| Groups | Count | Sum | Average | Variance |
|---|---|---|---|---|
| True Heart | 12 | 23.41818182 | 1.95152 | 0.014448 |
| Green Thunder | 12 | 17.95252525 | 1.49604 | 0.004053 |
| PIC Cos | 12 | 20.66666667 | 1.72222 | 0.017536 |

ANOVA

| Source of Variation | SS | df | MS | F | P-value | F crit |
|---|---|---|---|---|---|---|
| Between Groups | 1.2447445 | 2 | 0.62237 | 51.81151 | 6.6E−11 | 3.284924 |
| Within Groups | 0.3964039 | 33 | 0.01201 | | | |
| Total | 1.6411483 | 35 | | | | |

DEPOSIT INFORMATION

A deposit of the Synergene Seed & Technology, Inc. proprietary lettuce cultivar designated True Heart disclosed above and recited in the appended claims has been made with the American Type Culture Collection (ATCC), 10801 University Boulevard, Manassas, Va. 20110. The date of deposit was Aug. 27, 2008. The deposit of 2,500 seeds was taken from the same deposit maintained by Synergene Seed & Technology, Inc. since prior to the filing date of this application. All restrictions upon the deposit have been removed, and the deposit is intended to meet all of the requirements of 37 C.F.R. 1.801-1.809. The ATCC accession number is PTA-9437. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of lettuce cultivar True Heart, representative sample seed of said cultivar was deposited under ATCC Accession No. PTA-9437.

2. A lettuce plant, or a part thereof, produced by growing the seed of claim 1.

3. A tissue culture produced from protoplasts or cells from the plant of claim 2, wherein said cells or protoplasts of the tissue culture are produced from a plant part selected from the group consisting of leaf, pollen, embryo, cotyledon, hypocotyl, meristematic cell, root, root tip, pistil, anther, flower, shoot, stem, seed, and petiole.

4. A lettuce plant regenerated from the tissue culture of claim 3, wherein the plant has all of the morphological and physiological characteristics of cultivar True Heart.

5. A method for producing a lettuce seed comprising crossing two lettuce plants and harvesting the resultant lettuce seed, wherein at least one lettuce plant is the lettuce plant of claim 2.

6. A lettuce seed produced by the method of claim 5.

7. A lettuce plant, or a part thereof, produced by growing said seed of claim 6.

8. A method of producing a male sterile lettuce plant wherein the method comprises transforming the lettuce plant of claim 2 with a nucleic acid molecule that confers male sterility.

9. A male sterile lettuce plant produced by the method of claim 8.

10. A method of producing an herbicide resistant lettuce plant wherein the method comprises transforming the lettuce plant of claim 2 with a transgene wherein the transgene confers resistance to an herbicide selected from the group consisting of imidazolinone, sulfonylurea, glyphosate, glufosinate, L-phosphinothricin, triazine and benzonitrile.

11. An herbicide resistant lettuce plant produced by the method of claim 10.

12. A method of producing a pest or insect resistant lettuce plant wherein the method comprises transforming the lettuce plant of claim 2 with a transgene that confers pest or insect resistance.

13. A pest or insect resistant lettuce plant produced by the method of claim 12.

14. The lettuce plant of claim 13, wherein the transgene encodes a *Bacillus thuringiensis* endotoxin.

15. A method of producing a disease resistant lettuce plant wherein the method comprises transforming the lettuce plant of claim 2 with a transgene that confers disease resistance.

16. A disease resistant lettuce plant produced by the method of claim 15.

17. A method of producing a lettuce plant with a value-added trait, wherein the method comprises transforming the lettuce plant of claim 2 with a transgene encoding a protein selected from the group consisting of a ferritin, a nitrate reductase, and a monellin.

18. A lettuce plant with a value-added trait produced by the method of claim 17.

19. A method of introducing a desired trait into lettuce cultivar True Heart wherein the method comprises:

(a) crossing a True Heart plant, wherein a representative sample of seed was deposited under ATCC Accession No. PTA-9437, with a plant of another lettuce cultivar that comprises a desired trait to produce progeny plants wherein the desired trait is selected from the group consisting of male sterility, herbicide resistance, insect or pest resistance, modified bolting and resistance to bacterial disease, fungal disease or viral disease;

(b) selecting one or more progeny plants that have the desired trait to produce selected progeny plants;

(c) crossing the selected progeny plants with the True Heart plants to produce backcross progeny plants;

(d) selecting for backcross progeny plants that have the desired trait and all of the physiological and morphological characteristics of lettuce cultivar True Heart listed in Table 1; and (e) repeating steps (c) and (d) three or more times in succession to produce selected fourth or higher backcross progeny plants that comprise the desired trait and all of the physiological and morphological characteristics of lettuce cultivar True Heart listed in Table 1.

20. A lettuce plant produced by the method of claim 19, wherein the plant has the desired trait.

21. The lettuce plant of claim 20, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

22. The lettuce plant of claim 20, wherein the desired trait is insect or pest resistance and the insect or pest resistance is conferred by a transgene encoding a *Bacillus thuringiensis* endotoxin.

* * * * *